(12) United States Patent
Kouznetsov

(10) Patent No.: US 7,399,859 B1
(45) Date of Patent: Jul. 15, 2008

(54) METHOD FOR CATALYTIC PREPARATION OF HYDROMORPHONE AND HYDROCODONE

(75) Inventor: Vladimir Kouznetsov, Cody, WY (US)

(73) Assignee: Cody Laboratories Inc., Cody, WY (US)

( * ) Notice: Subject to any disclaimer, the term of this patent is extended or adjusted under 35 U.S.C. 154(b) by 0 days.

(21) Appl. No.: 11/671,962

(22) Filed: Feb. 6, 2007

(51) Int. Cl.
*C07D 489/02* (2006.01)
*C07D 489/00* (2006.01)

(52) U.S. Cl. .............................. 546/45; 546/44; 546/46

(58) Field of Classification Search ................... 546/45, 546/44, 46
See application file for complete search history.

(56) References Cited

U.S. PATENT DOCUMENTS

| | | | | |
|---|---|---|---|---|
| 2,544,291 | A | 3/1951 | Baizer | 546/45 |
| 2,577,947 | A | 12/1951 | Baizer | 546/45 |
| 6,512,117 | B1 | 1/2003 | Harclerode | 546/45 |
| 6,589,960 | B2 | 7/2003 | Harclerode | 514/282 |
| 7,323,565 | B2 * | 1/2008 | Wang et al. | 546/45 |
| 2005/0124811 | A1 | 6/2005 | Wang | 546/44 |

FOREIGN PATENT DOCUMENTS

| | | | | |
|---|---|---|---|---|
| DE | 365 683 | 12/1922 | ..................... | 12/14 |
| DE | 380 919 | 9/1923 | ..................... | 12/14 |
| DE | 607 931 | 1/1935 | ..................... | 12/14 |
| DE | 617 238 | 10/1935 | ..................... | 12/14 |
| DE | 623 821 | 1/1936 | ..................... | 12/14 |
| WO | WO 98/05667 | 2/1998 | | |
| WO | WO 2005/100361 | 10/2005 | | |

OTHER PUBLICATIONS

Kashiwabara, et al., "Chiral recognition in catalytic hydrogenation of α-acrylaminoacrylic acids by cationic rhodium (I) complexes of chiral aminophosphines derived from (R,R)-1,2-cyclohexanediamine or (R)-1,2-propanediamine" *J. Bull. Chem. Soc. Jpn.* 1980, 53, 2275.

McGrath, et al., "The mechanism of aqueous ruthenium (II)-catalyzed olefin isomerization" *Organometallics*, 1994, 13, 224.

Svoboda et al., "Reduction of substituted cyclohexanones by 2-propanol in the presence of aminophosphine-rhodium(I) complexes" Coll. Czech. Chem. Commun. 1977, 42(7), 2177.

\* cited by examiner

*Primary Examiner*—Charanjit S Aulakh
(74) *Attorney, Agent, or Firm*—Merchant & Gould, P.C.

(57) ABSTRACT

The present invention generally relates to catalysts of formula (III)

$$[M(P(R_a)(R_b)N(R_c)(R_d))_2X_n]_mY_p$$

that selectively convert morphine/codeine to hydromorphone/hydrocodone, and methods of use thereof.

11 Claims, No Drawings

METHOD FOR CATALYTIC PREPARATION OF HYDROMORPHONE AND HYDROCODONE

BACKGROUND OF THE INVENTION

Hydromorphone and hydrocodone are semi-synthetic narcotics used as analgesics and antitussive drugs. Both compounds can be prepared by transition metal catalyzed isomerization of morphine and codeine, respectively.

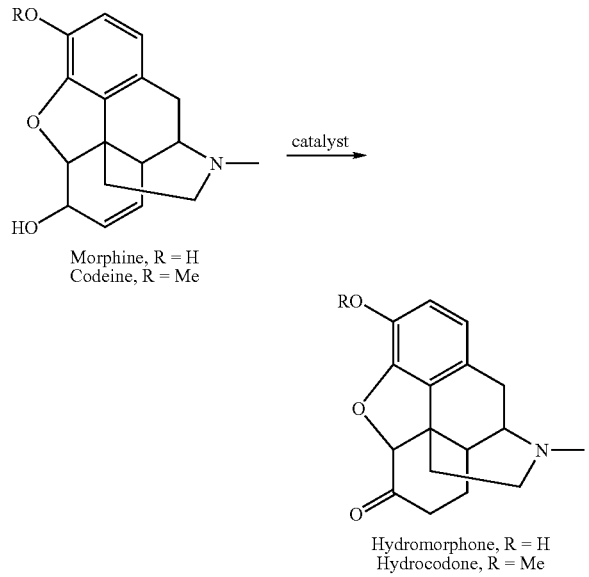

Morphine, R = H
Codeine, R = Me

Hydromorphone, R = H
Hydrocodone, R = Me

Application of heterogeneous catalysts such as finely divided Pt and Pd or Pt, Pd and Ru anchored to solid supports for this transformation was disclosed in a number of patents (DE 365 683, DE 380 919, DE 607 931, DE 617 238, DE 623 821, U.S. Pat. No. 2,544,291, U.S. Pat. No. 2,577,947, U.S. Pat. No. 6,512,117, U.S. Pat. No. 6,589,960, WO 2005/100361). Unfortunately, the described heterogeneous catalysts often demonstrate low selectivity, which results in low yield of the desired product and/or tedious purification procedures.

Isomerization of allylic alcohols to the corresponding ketones catalyzed by soluble transition metal complexes is a well documented process (see, for example, McGrath, et al. *Organometallics*, 1994, 13, 224 and references cited therein). However, despite the fact that morphine and codeine are allylic alcohols, there are only few known examples of successful application of homogeneous catalysis for the isomerization of these compounds to hydromorphone and hydrocodone (WO 98/05667, US 2005/0124811 A1).

Thus, a need exists for new catalysts capable of converting morphine/codeine to hydromorphone/hydrocodone.

SUMMARY OF THE INVENTION

The present invention provides novel highly active homogeneous catalysts, which selectively convert morphine and codeine to hydromorphone and hydrocodone, respectively. The catalysts are generally of the formula (III):

wherein M is selected from Rh and Ir; each $R_a$, $R_b$, $R_c$ and $R_d$ is independently selected from H, optionally substituted alkyl, and optionally substituted aryl, heterocylic, or cycloalkyl; each X is independently H, —OH, halo, alkoxide, aryloxide, an anion or solvent molecule; Y is an anion; n is 0 or 1; m is 1 or 2; and p is 0, 1 or 2. In addition $R_a$ and $R_b$ and/or $R_c$ and $R_d$ may be connected to form a chain or form an optionally substituted cycloalkyl or heterocyclic ring system.

Preferred compounds are catalysts of formula (IV):

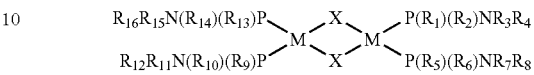

wherein M is Rh and Ir;

X is H, —OH, halo, alkoxide, aryloxide, an anion or solvent molecule;

$R_1$, $R_2$, $R_5$, $R_6$, $R_9$, $R_{10}$, $R_{13}$ and $R_{14}$ are independently selected from H or optionally substituted aryl, heterocylic, or cycloalkyl;

$R_3$, $R_4$, $R_7$, $R_8$, $R_{11}$, $R_{12}$, $R_{15}$ and $R_{16}$ are independently selected from H and optionally substituted alkyl; or $R_4$ and $R_8$ and/or $R_{12}$ and $R_{16}$ may be connected to form a chain or form an optionally substituted cycloalkyl or heterocyclic ring system; and salts and ions thereof.

The present invention further provides methods of synthesizing catalysts of formulas (III) and (IV), and methods of use in transforming morphine and codeine. The catalysts may also be used to isomerize other allylic alcohols to their corresponding ketones.

DETAILED DESCRIPTION OF THE INVENTION

As used herein, "alkyl" refers to straight or branched chain alkyl groups having one or more carbon atoms which may be saturated, unsaturated or partially unsaturated; "substituted alkyl" refers to alkyl groups further bearing one or more substituents such as hydroxy, alkoxy, mercapto, aryl, heterocyclic, halogen, trifluoromethyl, cyano, nitro, amino, carboxyl, carbamate, sulfonyl, sulfonamide and the like;

"cycloalkyl" refers to cyclic ring-containing groups containing in the range of 3 to 14 carbon atoms in the ring system, which may be a fused or an unfused single ring system, which may be saturated, or partially unsaturated, and "substituted cycloalkyl" refers cycloalkyl groups further bearing one or more substituents as set forth above;

"aliphatic" refers to saturated or unsaturated carbon groups which may be arranged in straight or branched chain arrangements of carbon atoms;

"aryl" refers to aromatic ring systems having 6 to 14 carbon atoms in the ring system, (which may be fused such as in napthylene, anthracene, or phenanthrene), and "substituted aryl" refers to aryl groups further bearing one or more substituents as set forth above;

"heterocyclic" refers to cyclic (i.e., ring-containing) groups, which may be fused, containing one or more heteroatoms (e.g., N, O, S, or the like) as part of the ring structures, and having 3 to 14 carbon atoms in the ring system, which may be saturated, unsaturated or partially unsaturated, and "substituted heterocyclic" refers to heterocyclic groups further bearing one or more substituents as set forth above; and "halogen" refers to fluoride, chloride, bromide, or iodide groups.

The present invention generally relates to catalysts for use in catalyzing the transformation of morphine and codeine to hydromorphone and hydrocodone, respectively. Compounds for use in practicing the invention include those of formula (III):

wherein M is a group VIII transition metal such as Rh and Ir; each $R_a$, $R_b$, $R_c$ and $R_d$ is independently selected from H, $C_{1-12}$ alkyl optionally substituted with halo and —OH; and aryl, cycloalkyl and heterocyclic each optionally substituted with halo, —OH or $C_{1-4}$ alkyl; each X is independently H, —OH, halo, alkoxide, aryloxide, an anion or a solvent molecule; Y is an anion; n is 0 or 1; m is 1 or 2; and p is 0, 1 or 2.

In one embodiment, each $R_a$ and $R_b$ is independently selected from optionally substituted aryl, heterocyclic, and cycloalkyl and may be connected to form a chain or form an optionally substituted cycloalkyl or heterocyclic ring system and each $R_c$ and $R_d$ is independently selected from H and optionally substituted $C_{1-8}$ alkyl, preferably $C_{1-4}$ alkyl and may be connected to form a chain or form an optionally substituted cycloalkyl or heterocyclic ring system.

Preferred halo atoms are Cl, I and Br. Preferably, M is Rh. Typical anions include $BF_4$, $PF_6$, $ClO_4$, $CHO_2$, $C_2O_4$, $CF_3CO_2$, $CF_3SO_3$, $CH_3CO_2$, $ArCO_2$, $CH_3SO_3$, $OCOCF_3$, p-tolylSO$_3$, $HSO_4$ and $H_2PO_4$.

Preferred catalysts include those of formula (IV):

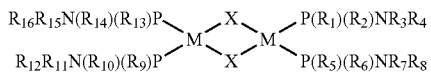

wherein M is selected from the group consisting of Rh and Ir;

each X is independently H, —OH, halo, alkoxide, aryloxide, an anion or a solvent molecule;

$R_1$, $R_2$, $R_5$, $R_6$, $R_9$, $R_{10}$, $R_{13}$ and $R_{14}$ are independently selected from H and aryl, heterocyclic, or cycloalkyl each optionally substituted with halo, —OH or $C_{1-4}$ alkyl;

$R_3$, $R_4$, $R_7$, $R_8$, $R_{11}$, $R_{12}$, $R_{15}$ and $R_{16}$ are independently selected from H, $C_{1-12}$ alkyl optionally substituted with halo or —OH; where optionally $R_4$ and $R_8$ together, and $R_{12}$ and $R_{16}$ together form an cycloalkyl, heterocyclic or aryl ring system selected from C, N, S and O; said ring system optionally substituted with halo, —OH or $C_{1-4}$ alkyl; and salts and ions thereof.

In one preferred embodiment, $R_1$, $R_2$, $R_5$, $R_6$, $R_9$, $R_{10}$, $R_{13}$ and $R_{14}$ are independently selected from H or $C_{5-6}$ aryl, optionally substituted with halo, —OH or $C_{1-4}$ alkyl. In another, $R_3$, $R_4$, $R_7$, $R_8$, $R_{11}$, $R_{12}$, $R_{15}$ and $R_{16}$ are H, $C_{1-8}$ alkyl optionally substituted with halo or —OH. In a further embodiment, at least one of $R_4$ and $R_8$, and $R_{12}$ and $R_{16}$ form a cycloalkyl, heterocyclic or aryl ring system comprising atoms selected from C, N, S and O; said ring system optionally substituted with halo, —OH or $C_{1-4}$ alkyl. In yet another embodiment, each of $R_4$ and $R_8$, and $R_{12}$ and $R_{16}$ form an cycloalkyl, heterocyclic or aryl ring system comprising atoms selected from C, N, S and O; said ring system optionally substituted with halo, —OH or $C_{1-4}$ alkyl. In a particular embodiment, $R_1$, $R_2$, $R_5$, $R_6$, $R_9$, $R_{10}$, $R_{13}$ and $R_{14}$ are each phenyl; $R_3$, $R_7$, $R_{11}$, and $R_{15}$ are each $CH_3$; and $R_4$ and $R_8$ together, and $R_{12}$ and $R_{16}$ together each form a $C_6$ cycloalkyl ring. In another particular embodiment, $R_1$, $R_2$, $R_5$, $R_6$, $R_9$, $R_{10}$, $R_{13}$ and $R_{14}$ are each phenyl; and $R_3$, $R_4$, $R_7$, $R_8$, $R_{11}$, $R_{12}$, $R_{15}$ and $R_{16}$ are each $C_2H_5$.

The catalysts for this process are conveniently prepared by treatment of commercially available ethylene or cyclooctene (COE) rhodium complexes with two (2) molar equivalents of various aminophosphines in a suitable solvent and can be used in situ.

Exemplary aminophosphines are shown below where $R_1$, $R_2$, $R_3$, $R_4$, $R_5$, $R_6$, $R_7$, $R_{17}$ are each independently selected from optionally substituted aryl, heterocyclic, and cycloalkyl, Z is selected from $CR_1R_2$, O, $NR_3$, S, and n and m are each 0 to 10.

Aminophosphines

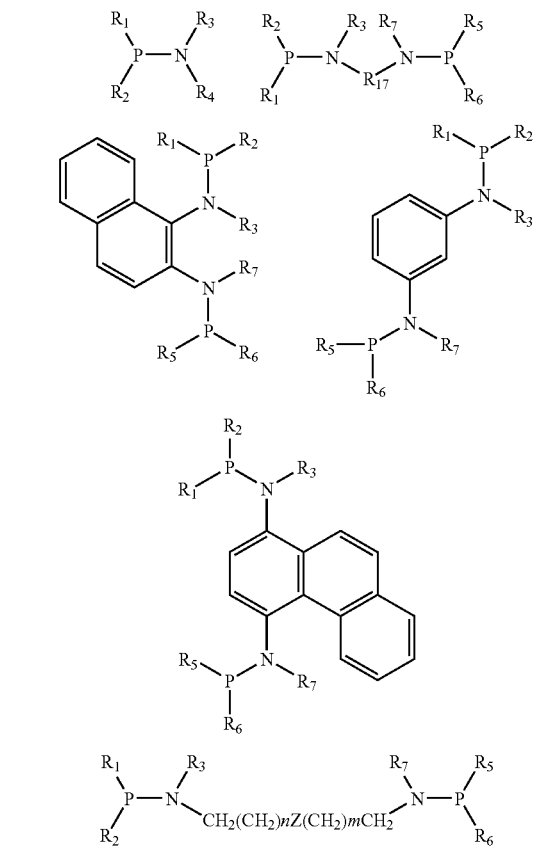

Exemplary aminophosphines may be prepared as shown in the scheme below,

Preparation of Aminophosphines

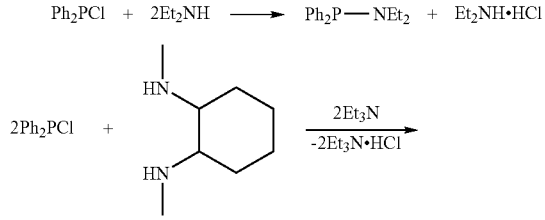

-continued

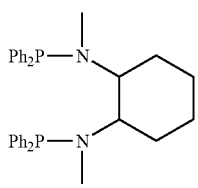

Preparation of Rhodium-Aminophosphine Complexes

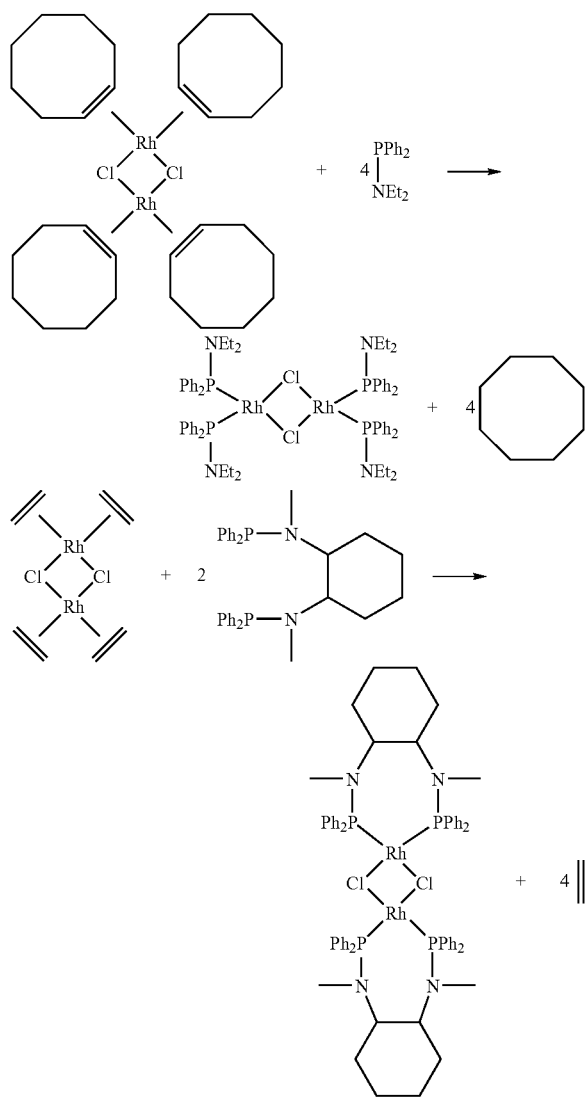

Thus, the catalysts are typically prepared by reacting a suitable rhodium precursor such as chlorobis(ethylene)rhodium(I) dimer [ClRh(C$_2$H$_4$)$_2$]$_2$ or chlorobis(cyclooctene)rhodium(I) dimer [ClRh(COE)$_2$]$_2$ with an aminophosphine of the formula P(R$_a$)(R$_b$)N(R$_c$)(R$_d$), wherein R$_a$, R$_b$, R$_c$ and R$_d$ are as defined above. See, Svoboda et al., Coll. Czech. Chem. Commun. 1977, 42(7), 2177, incorporated herein by reference.

In one method, morphine/codeine is transformed to hydromorphone/hydrocodone in the presence of at least one catalyst of the present invention. Isomerization of morphine can optionally be done in the presence of a strong base such as NaOMe, which deprotonates the phenolic moiety of morphine/hydromorphone and thus increases the solubility of these species in the reaction mixture. Complete isomerization of morphine/codeine normally requires less then 1 hour in boiling methanol when 1 mol % of these catalysts is used. Isolation procedure is exceptionally simple and provides pure products in high yield.

The following examples are given to illustrate the preparation of the catalysts and its use for the preparation of hydromorphone and hydrocodone.

EXAMPLE 1

Preparation of Diphenylphosphinodiethylamine

All operations were carried out in a nitrogen atmosphere using standard Schlenk technique. Toluene was distilled under nitrogen from benzophenone-sodium. Other chemicals were purchased from Strem Chemicals or Aldrich and used as received.

Diphenylchlorophosphine (2.0 mL, 2.38 g, 10.79 mmol) was added to a stirred solution of diethylamine (2.5 mL, 1.82 g, 24.9 mmol) in toluene (20 mL). The resulting white slurry was stirred overnight at ambient temperature and filtered. The filtered solid was washed with toluene (2×10 mL). The combined filtrate was reduced in volume by distillation in vacuum to approximately 20 mL and transferred to a graduated Schlenk tube equipped with a Yong valve. The volume of the solution was adjusted to 31.0 mL by addition of toluene to give 0.348 M solution of Ph$_2$PNEt$_2$. $^{31}$P{$^1$H} NMR (toluene, 25° C.), δ: 51.0 (s).

EXAMPLE 2

Preparation of trans-1,2-(N,N'-bisdiphenylphosphino-N,N'-dimethylamino)cyclohexane The compound was prepared by slight modification of the reported procedure (Kashiwabara, et al., J. Bull. Chem. Soc. Jpn. 1980, 53, 2275). Unless other specified all operations were carried under an air atmosphere. Dry tetrahydrofurane (THF) and hexane were prepared by distillation from benzophenone-sodium under nitrogen. Other chemicals were purchased from Strem Chemicals or Aldrich and used as received.

Stirred mixture of trans-1,2-diaminocyclohexane (10.0 g, 87.6 mmol), THF (150 mL) water (120 mL) and potassium carbonate (40 g) was cooled to 5° C. and treated with ethyl chloroformate (35 mL, 39.9 g, 367 mmol). The mixture was stirred at ambient temperature for 4 hours, the upper layer was separated and the aqueous phase was extracted with THF (70 mL). The combined THF extract was evaporated to dryness. The residue was dissolved in dichloromethane. The solution was dried over potassium carbonate, filtered and evaporated to dryness. The obtained white solid was slurried in ether (70 mL), filtered, washed with pentane (2×80 mL) and dried in an oven at 90° C. for 2 hours to give 22.03 g (97% yield) of trans-1,2-bis(ethoxycarbonylamino)cyclohexane as a snow-white solid.

trans-1,2-bis(ethoxycarbonylamino)cyclohexane (22.0 g, 85.17 mmol) was added as a solid to a stirred mixture of dry THF (200 mL) and lithium aluminium hydride (12.0 g) cooled to 5° C. The resulting slurry was stirred under nitrogen at ambient temperature for 2 hours then heated to reflux overnight. The reaction mixture was cooled to 5° C. and treated carefully with water (24 mL) and then with 15% NaOH (18 mL). The resulting slurry was stirred at ambient temperature for 30 min, heated to reflux for 30 min and filtered while hot. The filtered solid was washed with THF (2×80 mL) and the combined filtrate was evaporated in vacuum. The residue was dissolved in pentane (100 mL), filtered through a short silica column and eluted with pentane (2×40 mL). The combined filtrate was evaporated in vacuum to give 10.3 g (88% yield) of trans-1,2-N,N'-dimethylaminocyclohexane as a colorless oil.

From this point all operations were carried out in a nitrogen atmosphere using standard Schlenk technique.

Diphenylchlorophosphine (2.61 mL, 3.10 g, 14.06 mmol) was added to a stirred solution of triethylamine (3.0 mL, 2.18 g, 21.5 mmol) and trans-1,2-N,N'-dimethylaminocyclohexane (1.0 g, 7.03 mmol) in dry THF (20 mL). The resulting slurry was stirred overnight at ambient temperature and filtered. The filtered solid was washed with dry THF (2×10 mL). The combined filtrate was evaporated under vacuum to ca 5 mL and diluted with dry hexane (20 mL). The formed solid was filtered, washed with dry hexane (2×10 mL) and dried in vacuum to afford trans-1,2-(N,N'-bisdiphenylphosphino-N, N'-dimethylamino)cyclohexane as a snow-white solid. The yield was 2.65 g (74%). $^{31}P\{^{1}H\}$ NMR ($C_6D_6$, 25° C.), δ: 61.7 (s). The compound was stored under air.

EXAMPLE 3

Preparation of Hydromorphone

Preparation of the catalyst was carried out under nitrogen using a standard Schlenk technique. Toluene was dried over sodium/benzophenone and distilled under nitrogen. Reagent grade methanol, acetic aid, sodium methoxide and chlorobis (ethylene) rhodium (I) dimer were purchased from Aldrich or Strem Chemicals and used as received.

Trans-1,2-(N,N'-Bisdiphenylphosphino-N,N'-dimethylamino)cyclohexane (86 mg, 0.167 mmol) was added to a solution of $[ClRh(C_2H_4)_2]_2$ (33 mg, 0.167 mga Rh) in toluene (4 mL). The mixture was stirred for 15 min to give a dark orange solution of the catalyst.

A 100 mL Schlenk tube was charged with methanol (50 mL), morphine free base (5.0 g, 17.52 mmol) and sodium methoxide (47.4 mg, 0.876 mmol). The mixture was stirred and heated to reflux under nitrogen for 15 min then treated with the solution of the catalyst added by a pipette. The resulting brown solution was stirred and heated to reflux under nitrogen for 1 hour, cooled to 7° C. in an ice bath, treated with acetic acid (0.05 mL, 0.876 mmol), stirred for another 30 min and filtered. The filtered solid was washed with isopropanol (3×8 mL) and dried in an oven at 95° C. to give hydromorphone free base as a white solid. The yield was 4.12 g, 82.4%.

HPLC analysis: dihydromorphine—below detection limit (≦0.01%), morphine—below detection limit (≦0.01%), morphinone—below detection limit (≦0.01%), hydromorphone—100%.

EXAMPLE 4

Preparation of Hydrocodone

Preparation of the catalyst was carried out under nitrogen using a standard Schlenk technique. Toluene was dried over sodium/benzophenone and distilled under nitrogen. Reagent grade methanol and chlorobis(cyclooctene)rhodium (I) dimer were purchased from Aldrich or Strem Chemicals and used as received.

Diphenylphosphinodiethylamine (0.48 mL, 0.348 M in toluene, 0.167 mmol) was added to a suspension of $[ClRh (COE)_2]_2$ (60 mg, 0.167 mga Rh) in toluene (4 mL). The mixture was stirred for 15 min to give a dark orange solution of the catalyst.

A 100 mL Schlenk tube was charged with methanol (30 mL) and codeine free base (5.3 g, 17.7 mmol). The stirred solution was heated to reflux under nitrogen for 15 min and treated with the solution of the catalyst added by a pipette. The resulting brown solution was stirred and heated to reflux under nitrogen for 1 hour, cooled to 7° C. in an ice bath, stirred at this temperature for another 30 min and filtered. The filtered solid was washed with cold isopropanol (3×6 mL) and dried in an oven at 95° C. to give hydrocodone free base as a white solid. The yield was 4.48 g, 84.5%.

HPLC analysis: dihydrocodeine—below detection limit (≦0.01%), codeine—0.02%, codeinone—below detection limit (≦0.01%), hydrocodone—99.98%.

EXAMPLE 5

Preparation of Hydromorphone

Preparation of the catalyst was carried out under nitrogen using a standard Schlenk technique. Toluene was dried over sodium/benzophenone and distilled under nitrogen. Reagent grade methanol and chlorobis(cyclooctene)rhodium (I) dimer were purchased from Aldrich or Strem Chemicals and used as received.

Diphenylphosphinodiethylamine (4.80 mL, 0.348 M in toluene, 1.67 mmol) was added to a suspension of $[ClRh (COE)_2]_2$ (600 mg, 1.67 mga Rh) in toluene (10 mL). The mixture was stirred for 15 min to give a dark orange solution of the catalyst.

A 1 L round bottom flask equipped with return condenser and nitrogen inlet was charged with methanol (650 mL) and morphine free base (50.0 g, 175.2 mmol). The mixture was stirred magnetically and heated to reflux under nitrogen until all morphine dissolves (45 min) then treated with the solution of the catalyst added via a cannula. The resulting brown solution was stirred and heated to reflux under nitrogen for 1 hour, then volume of the mixture was reduced to ca 400 mL by distillation. The resulting slurry was cooled to 7° C. in an ice bath, stirred at this temperature for 1 hour and filtered. The filtered solid was washed with isopropanol (3×60 mL) and dried in an oven at 95° C. to give hydromorphone free base as a white solid. The yield was 41.71 g, 83.4%.

HPLC analysis: dihydromorphine—below detection limit (≦0.01%), morphine—0.46%, morphinone—0.03, hydromorphone—99.51%.

I claim:

1. A method of transforming morphine to hydromorphone or codeine to hydrocodone in the presence of a compound of formula (III):

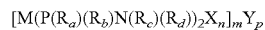

wherein M is Rh or Ir;

each $R_a$, $R_b$, $R_c$ and $R_d$ is independently H, optionally substituted alkyl, aryl, heterocyclic, or cycloalkyl;

each X is independently H, —OH, halo, alkoxide, aryloxide, an anion or a solvent molecule;

Y is an anion; n is 0 or 1; m is 1 or 2; and p is 0, 1 or 2.

2. The method of claim 1 wherein
M is Rh;

each $R_a$, $R_b$, $R_c$ and $R_d$ is independently selected from H, $C_{1-8}$ alkyl optionally substituted with halo or —OH; and aryl, heterocyclic, or cycloalkyl; each optionally substituted with halo, —OH or alkyl; and each X is independently H, OH or halide.

3. A method of transforming morphine to hydromorphone or codeine to hydrocodone in the presence of a compound of the formula:

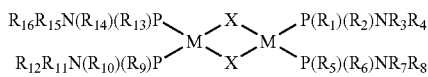

wherein M is Rh or Ir;

each X is independently H, —OH, halo, alkoxide, aryloxide, an anion or a solvent molecule;

$R_1$, $R_2$, $R_5$, $R_6$, $R_9$, $R_{10}$, $R_{13}$ and $R_{14}$ are independently selected from H and optionally substituted aryl, heterocyclic, or cycloalkyl;

$R_3$, $R_4$, $R_7$, $R_8$, $R_{11}$, $R_{12}$, $R_{15}$ and $R_{16}$ are independently selected from H and optionally substituted alkyl; or $R_4$ and $R_8$, and $R_{12}$ and $R_{16}$ form an optionally substituted cycloalkyl, heterocyclic, or aryl ring system.

4. The method of claim 3 wherein $R_1$, $R_2$, $R_5$, $R_7$, $R_9$, $R_{10}$, $R_{13}$ and $R_{14}$ are independently selected from H and aryl, heterocyclic, or cycloalkyl, each optionally substituted with halo, —OH or $C_{1-4}$ alkyl;

$R_3$, $R_4$, $R_6$, $R_8$, $R_{11}$, $R_{12}$, $R_{15}$ and $R_{16}$ are independently selected from H, $C_{1-8}$ alkyl optionally substituted with halo or —OH; or $R_4$ and $R_8$, and $R_{12}$ and $R_{16}$ form an cycloalkyl, heterocyclic or aryl ring system comprising C, N, S and O; said ring system optionally substituted with halo, —OH or $C_{1-4}$ alkyl.

5. The method of claim 4 wherein $R_1$, $R_2$, $R_5$, $R_6$, $R_9$, $R_{10}$, $R_{13}$ and $R_{14}$ are independently selected from H or $C_{5-6}$ aryl, optionally substituted with halo, —OH or $C_{1-4}$ alkyl.

6. The method of claim 4 wherein $R_3$, $R_4$, $R_7$, $R_8$, $R_{11}$, $R_{12}$, $R_{15}$ and $R_{16}$ are H or $C_{1-8}$ alkyl optionally substituted with halo or —OH.

7. The method of claim 4 wherein $R_4$ and $R_8$, and/or $R_{12}$ and $R_{16}$ form an cycloalkyl, heterocyclic or aryl ring system comprising atoms selected from C, N, S and O; said ring system optionally substituted with halo, —OH or $C_{1-4}$ alkyl.

8. The method of claim 7 wherein each of $R_4$ and $R_8$, and $R_{12}$ and $R_{16}$ form an cycloalkyl, heterocyclic or aryl ring system comprising 3 to 8 atoms selected from C, N, S and O; said ring system optionally substituted with halo, —OH or $C_{1-4}$ alkyl.

9. The method of claim 8 wherein each of $R_4$ and $R_8$, and $R_{12}$ and $R_{16}$ form an cycloalkyl, heterocyclic or aryl ring system comprising 5 to 6 atoms selected from C, N, S and O; said ring system optionally substituted with halo, —OH or $C_{1-4}$ alkyl.

10. The method of claim 9 wherein each of $R_4$ and $R_8$, and $R_{12}$ and $R_{16}$ form an cycloalkyl ring system comprising 5 to 6 C atoms; said ring system optionally substituted with halo, —OH or $C_{1-4}$ alkyl.

11. A method for transforming morphine to hydromorphone or codeine to hydrocodone comprising reacting a compound of the formula $[ClRh(C_2H_4)_2]_2$ or $[ClRh(COE)_2]_2$ with a compound of the formula $P(R_a)(R_b)N(R_c)(R_d)$; wherein each $R_a$, $R_b$, $R_c$ and $R_d$ is independently selected from H, optionally substituted alkyl; and optionally substituted aryl, heterocyclic, or cycloalkyl; COE is cyclooctene; and adding the resulting product to a solution containing morphine or codeine; and reacting the mixture to transform morphine to hydromorphone or codeine to hydrocodone.

* * * * *